United States Patent [19]
White

[11] Patent Number: 4,772,283
[45] Date of Patent: Sep. 20, 1988

[54] CORNEAL IMPLANT

[76] Inventor: Thomas C. White, 1701 S. Minnesota Ave., Sioux Falls, S. Dak. 57105-1765

[21] Appl. No.: 130,748

[22] Filed: Dec. 9, 1987

Related U.S. Application Data

[63] Continuation-in-part of Ser. No. 864,022, May 16, 1986, abandoned.

[51] Int. Cl.$^4$ .............................................. A61F 2/14
[52] U.S. Cl. ...................................................... 623/5
[58] Field of Search .................................. 623/5, 6, 1

[56] References Cited

U.S. PATENT DOCUMENTS

| 2,714,721 | 8/1955 | Stone | 623/5 |
| 3,562,820 | 2/1971 | Braun | 623/1 |
| 4,563,779 | 1/1986 | Helman | 623/5 |

OTHER PUBLICATIONS

"Corneal Surgery" (Boch), by L. J. Girard, Advanced Techniques in Ophthalmic Microsurgery, vol. 2, 1981, pp. 32, 144, 145, 154, 155, 168–171.

Primary Examiner—Richard J. Apley
Assistant Examiner—James Prizant
Attorney, Agent, or Firm—Gregory P. Kaihoi; James R. Haller; Mary P. Bauman

[57] ABSTRACT

An implant prosthesis for replacing a full or partial thickness of a cornea. Prosthesis includes a transparent lens portion, and a carrier of preserved, denatured tissue. The lens is attached to the carrier which in turn is adapted for attachment to the eye wall.

11 Claims, 5 Drawing Sheets

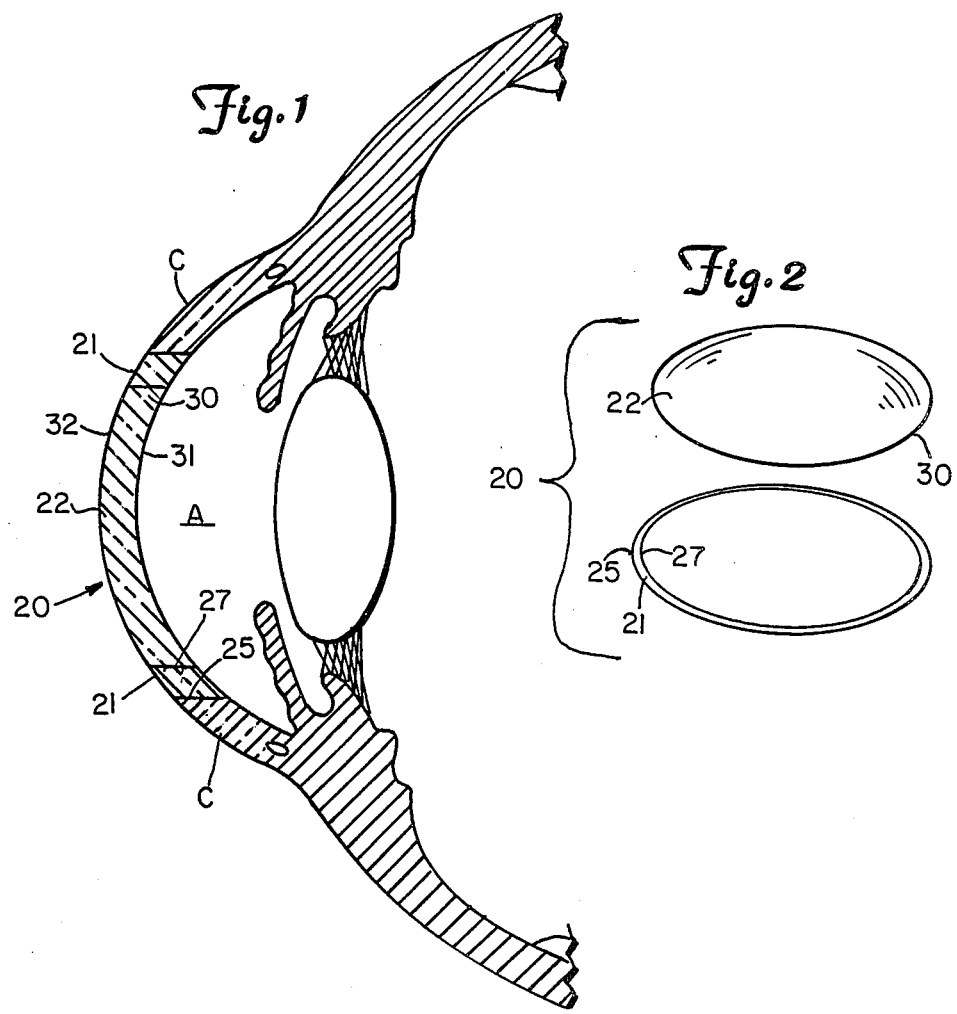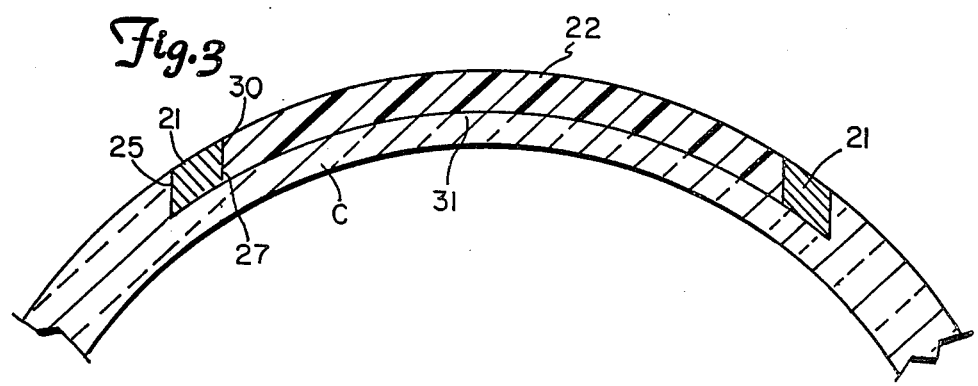

CORNEAL IMPLANT

This application is a continuation-in-part of Ser. No. 6/864,022, filed May 16, 1986, now abandoned.

FIELD OF THE INVENTION

This invention relates to prosthetic devices, and particularly to such devices as may be employed to replace damaged corneal tissue.

BACKGROUND OF THE INVENTION

For various reasons, the corneal portions of eyes must be surgically repaired or replaced. For example, the cornea may become scratched or scarred or otherwise physically damaged, greatly hindering sight. The cornea is also subject to the effects of various degenerative diseases, mandating replacement if the patient is to have normal or even near normal vision. Corneal transplants have become quite common in the United States, particularly with the advent of microsurgery. Unfortunately, donor corneas are very difficult to obtain. A cornea to be donated must be employed, if at all, within a matter of days or weeks from the time of death of the donor. Although eye banks have been organized throughout the United States, one cannot rely upon the availability of a donor at the time it is needed for a transplant operation. As a result, vision, which could have been wholly or partially restored in many patients, is often permanently lost. Furthermore, some diseases are not amenable to standard corneal transplants, and corneal transplants carry the constant risk of transmission of diseases carried in the transplanted tissue, including leukemia, syphilis, and Acquired Immunodeficiency Syndrome (AIDS). See Fuji Kawa, et. al., "Human T-Cell Leukemia/Lymphotrophic Virus Type III in the Conjunctival Epithelium of Patient with AIDS," 100 *Amer. J. Opthal.* 507 (October 1985); Pepose et. al., "The Impact of the AIDS Epidemic on Corneal Transplantation," 100 *Amer. J. Opthal.* 610 (October 1985).

Attempts have been made in the past to utilize artificial materials for corneal transplants. Representative of such attempts are those reported in Barraquer, *Queratomileusis y Queraqofaquia, Instituto Barraquer de America Bogata, Col.* (1980); U.S. Pat. No. 3,945,054, issued Mar. 23, 1976, Fedorov, et. al., "Through Corneal Prosthesis and Method of In stalling Same"; and U.S. Pat. No. 3,458,870, issued Aug. 5, 1969, W. Stone, Jr., "Artificial Corneal Implants Having a Removable Lens Member."

For the most part, the implantation of artificial corneal materials has been at best a temporary stop-gap measure taken to seal the anterior chamber of the eye for a period of time until a donor cornea could be located for transplantation. As with other parts of the human body, the eye tends to reject and eject or extrude foreign materials during the healing process, with the result that the implantation of artificial corneas generally leads to loss by extrusion of the device, with further eye damage and leakage of aqueous humor from the anterior chamber. Attempts to affix artificial corneas to the cornea by adhesive typically fail because the living cells contacted by adhesive eventually die and slough off (necrosis), destroying the adhesive seal. Thus, the prior art devices have relied on elaborate mechanical attachment methods which are fraught with continued need for surgical revision, and have had short lived, limited success.

SUMMARY OF THE INVENTION

The invention relates to an ocular implant prosthesis having a transparent lenticule, and a carrier bonded thereto, the carrier comprising preserved tissue adapted for attachment to an eye. The prosthesis optionally may replace the full thickness of the eye wall, a partial thickness, or be placed on the surface of Bowman's membrane after removal of the epithelium. In one embodiment, the carrier comprises an annular ring, the outer periphery thereof being adapted for attachment to the eye wall, and the inner circumferential surface thereof being bonded to the transparent lenticule. In another embodiment, the lenticule is bonded to the anterior surface of the carrier. In a further embodiment, the lenticule is bonded to the posterior surface of the carrier. In yet a further embodiment, the carrier includes a generally disc shaped pocket coaxial with the carrier, the pocket being adapted to receive there within the lenticule. The preserved tissue may be any suitable tissue, but preferably is cornea, sclera, fascia, cartilage, tendon, or bone.

The invention also relates to a method of surgically repairing the cornea of an eye, comprising the steps of removing at least a partial, generally circular thickness of the eye wall, including corneal tissue; providing an ocular prosthesis having a trans parent lenticule of biologically acceptable material bonded to a carrier, the carrier comprising preserved tissue adapted for attachment to the eye wall; and surgically attaching the carrier to the eye wall covering the area from which tissue was removed.

The use of preserved tissue provides great advantages over the prior art in that such tissue may be bonded to any suitable lenticule material. Because the tissue itself is preserved, the extra cellular collagen architectural matrix will not be adversely affected by the adhesive process (generally the cells themselves will have been destroyed), and therefore necrosis does not occur. Another advantage of the preserved tissue is that it will become durably attached to the live tissue of the eye through in-growth of live fibroblastic cells from the patient recipient into the structural matrix of the preserved tissue. Further, the tissue may be pre-served in such a fashion as to absolutely prevent the transmission of diseases from the preserved tissue source to the recipient.

BRIEF DESCRIPTION OF THE DRAWINGS

FIG. 1 is a cross sectional view of the human eye showing a prosthesis of the invention implanted;

FIG. 2 is a perspective exploded view of a corneal prosthesis of the invention;

FIG. 3 is a partial cross-sectional view of the cornea of an eye showing lamellar implant of a modified embodiment of the invention;

BEST MODE FOR CARRYING OUT THE INVENTION

Figure 4:
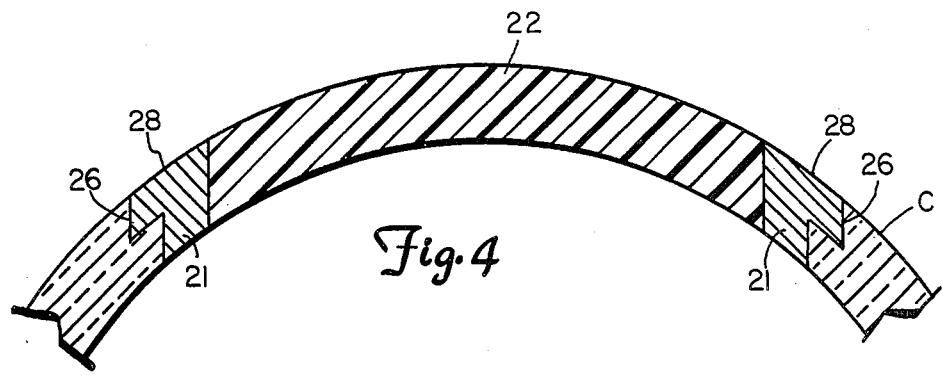
FIG. 4 is a cross-sectional view of a cornea showing a modified embodiment of the invention implanted.

FIGS. 1 and 2 depict the prosthesis of the invention generally as 20, including a central transparent lenticular portion 22 and a carrier 21. The prosthesis may be mounted in the eye as a corneal replacement as shown in the drawings, the carrier 21 spacing the lenticular portion 22 radially from the eye tissue.

The lenticule 22 may be made of any of a variety of suitable materials, including polymethyl methacrylate (PMMA), polycarbonates, HEMA, polysulfones, silicones and other substances that are biologically acceptable, not introducing harmful foreign substances into the eye. The lenticule 22 desirably has a slightly domed anterior surface 32 to simulate the natural curvature of the surgically removed corneal portion. Its posterior surface 31 may be configured as desired—convex, planar or concave. The lenticule 22 may be so configured as to act as a lens and to provide visual correction for the eye by varying the curvatures of the posterior 31 and anterior 32 surfaces.

The carrier 21 is constructed of preserved biological tissue. The tissue may be of any suitable material, including cornea, sclera, fascia or other connective tissues such as tendon, cartilage or bone. Corneal tissue is preferred for those embodiments shown in the drawing which require the carrier 21 to be transparent, for example, FIGS. 6–13, and 15. The tissue must be preserved in a fashion which generally maintains the structural integrity of the extra-cellular collagen architectural matrix. Such preservation processes include but are not necessarily limited to glycerin dehydration, alcohol preservation, gluteraldehyde preservation, and formalin preservation. Preferably the preservation process denatures the tissue, analogously to tanning of rawhide, resulting in a number of benefits as described below.

In a preferred method of preserving such tissue, biological tissue, such as sclera, is removed, cleaned, and placed into preservative such as gluteraldehyde or formalin, where it may be stored for a period of days, weeks, or even months. When desired, the tissue is removed from the preservative and, if not already in proper configuration, manufactured into the appropriate configuration. The tissue is then united with the artificial lenticule as described herein, and the resulting prosthesis is placed in a preservative that is compatible with the lenticule material such as formalin. It should be noted that some lenticule materials, such as PMMA, are incompatable with alcohol, but are compatable with other preservatives such as formalin, which is therefore a particularly preferred preservative for storage of the manufactured prosthesis. Desirably the preservative denatures the tissue. Denaturing may alter the antigenicity of the tissue to reduce or eliminate rejection complications, and in certain circumstances may permit use of biological tissue from other species. Denaturing also may tend to inhibit vascularization, a particularly desirable effect if the tissue is cornea. In most instances, the tissue is stored at least about three days in the preservative before use.

Manufacture of tissue into the appropriate physical configurations shown in the drawings can be accomplished by well known techniques including the use of microkeratomes and trephines. See, e.q., Kaufman, "The Correction of Aphakia," 89 American *Journal of Ophthalmology*, 1 (January 1980); Leigh, "Treatment of Gross Corneal Opacification by Lamellar and Annular Lamellar Keratoplasty," 39 *Brit. J. Ophthal.* 641 (1955); Waring, *Refractive Keratoplasty*, 31 Resident & Staff Physician, 25–34 (May, 1985).

FIG. 1 depicts the carrier 21 as having an outer periphery 25 and an inner circumferential surface 27 generally defined by coaxial cylinders. Other configurations may also be utilized, but the generally coaxially parallel configuration shown in FIG. 1 is particularly desirable due to its ease of manufacture using a trephine. Similarly, the periphery 30 of the lenticule 22 has a surface defined by a cylinder coaxially of the lenticule axis, thus providing surface-to-surface contact with the inner circumferential surface 27 of the carrier 21.

Figure 14:
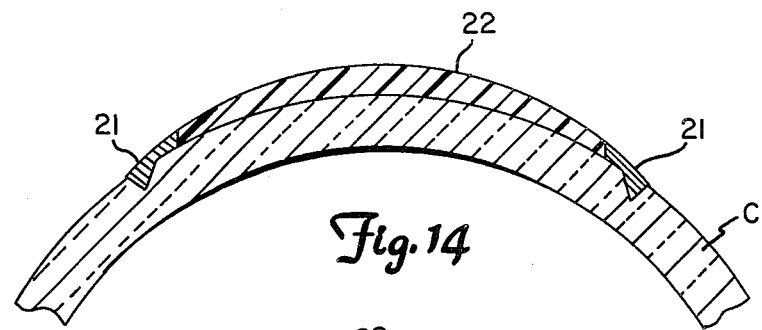
FIG. 14 is a partial cross-sectional view of the cornea of an eye showing lamellar implant of a modified embodiment of the invention.
Figure 15:
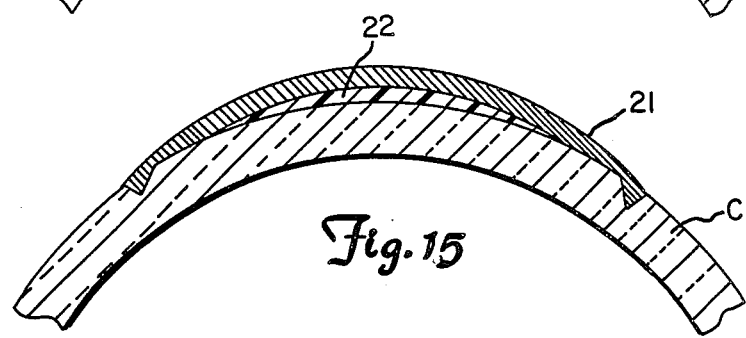
FIG. 15 is a partial cross-sectional view of the cornea of an eye showing lamellar implant of a modified embodiment of the invention.

FIG. 1 depicts replacement of the full thickness of the cornea (C). FIG. 2 depicts lamellar keratoplasty, i.e., replacement of only a partial thickness of the cornea (C). This technique has the advantage of not destroying the natural liquid seal of the cornea, and avoiding disruption of intraocular structures while replacing diseased or abnormal anterior corneal tissue. FIGS. 14–15 depict epikeratoplasty, i.e., placement of the prosthesis on the deepithelized surface of the cornea. Epikeratoplasty is particularly useful in the correction of myopia and hyperopia, as well as keratoconus and as a patch for perforations.

The lenticule 22 may be attached to the preserved tissue carrier 21 by any suitable means, including but not limited to any of a variety of biologically acceptable adhesives. Such adhesives must be characterized by their ability to form a liquid-tight bond between the material of the lenticule 22 and the preserved tissue carrier 21. Among adhesives suitable for this purpose are various well known dental adhesives. In particular, applicant has used adhesives sold by Johnson & Johnson under the product number 2748. This two part adhesive has successfully bonded both formalin and gluteraldehyde preserved tissue to a polymethyl methacrylate lenticule. Other methods of forming an adhesive bond between the lenticule and the preserved tissue may be utilized, including the use of heat and pressure.

Figure 16:
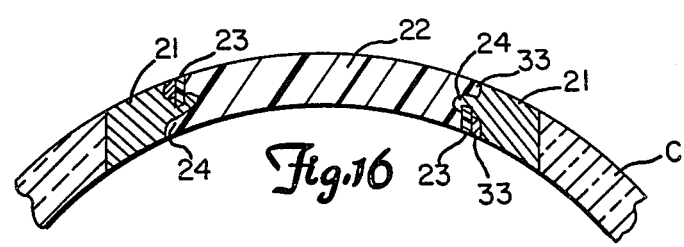
FIG. 16 is a partial cross-sectional view of the cornea of an eye showing a modified embodiment of the invention.
Figure 17:
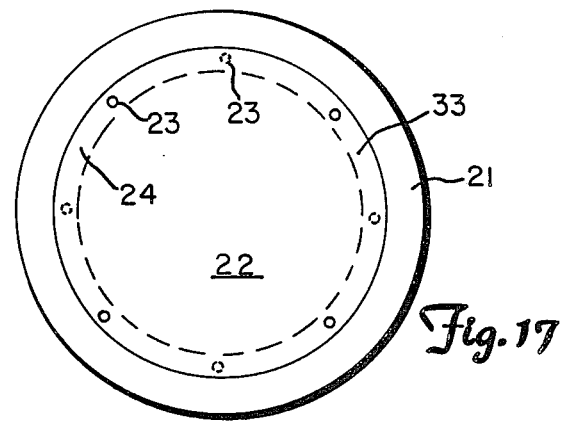
FIG. 17 is a plan view of the embodiment of FIG. 16.

FIGS. 16 and 17 depict a particularly preferred method of attaching the carrier to the lenticule 22. In this embodiment, the carrier 21 includes a radially inwardly extending flange 24 received in a complimentary groove in the peripheral edge of the lenticule. A plurality of axially extending stakes 23 are positioned about the periphery of the lenticule, the stakes 23 being driven at least part way through from one side of the lenticule into the flange 24 of the carrier 21. Desirably the stakes penetrate at least half way through the tissue flange 24.

To assemble such a prosthesis, the tissue may be rehydrated and placed about the lenticule. Stakes are then driven into place and, e.g., heat fused to the lenticule, the stakes desirably being of the same material as the lenticule. The unit is then placed in preservative, which frequently causes slight tissue shrinkage, resulting in a firm seal between the carrier 21 and the lenticule 22. The drawing shows eight generally equi-angularly spaced stakes. Any suitable number may be utilized, so long as enough are used to avoid undue stress on tissue surrounding any one stake. The stakes may be inserted from alternate sides of the lenticule, as shown in the drawings, or they may be inserted from a single side. If inserted from a single side, it is desirable that the stakes pass entirely through the carrier flange 24, thus being anchore in both opposing flanges 33 of the lenticule 22.

As an alternative to such stakes 23, the tissue may be retained in the peripheral groove of the lenticule by other similar mechanical means. Such means may comprise crimping the two flanges 33 of the lenticule to pinch and retain the carrier flange 24, either at selected points along the periphery of the lenticule (spaced similarly to the depicted spacing of the stakes 23) or along a continuous circumference. Point crimping may be preferred over continuous crimping, as the latter tends to deform the periphery of the lenticule more than point crimping.

Figure 5:
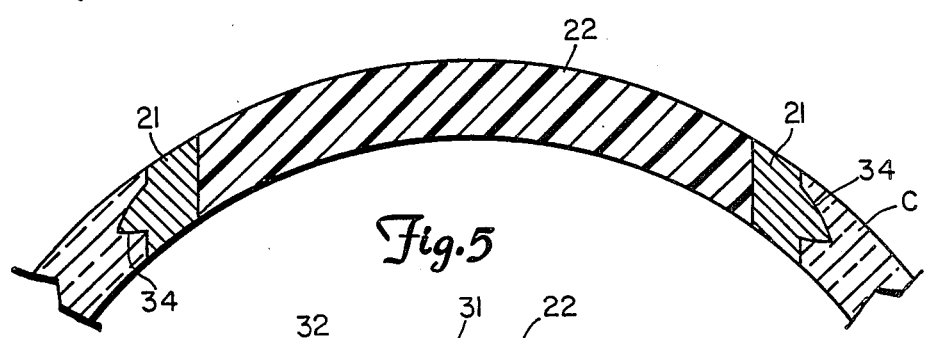
FIG. 5 is a cross-sectional view of a cornea showing a modified embodiment of the invention implanted.

FIGS. 4 and 5 depict, by way of example and not by way of limitation, alternative embodiments for the attachment of the carrier 21 to the cornea (C). In FIG. 4, the carrier is provided with a radially outwardly extending flange 26 at its anterior surface 28. The flange 26 is received in a complimentary groove formed in the cornea (C). This configuration is desirable for its natural structural assistance in placement of the prosthesis during surgery.

Figure 5 similarly shows a carrier having a radially outwardly extending flange 34 which is located approximately equidistant from the anterior and posterior surfaces of the prosthesis. The flange 34 is received within a complimentary annular groove formed in the cornea (C). Many of a variety of structural variations might be made to enhance attachment, including those described in my co-pending U.S. application, Ser. No. 402,740, now U.S. Pat. No. 4,612,012, which is hereby incorporated by reference. Similarly, the lenticule 22 may include flanges, protrusions, or other structural features to enhance attachment of the lenticule 22 to the carrier 21, e.g., as described above. For the sake of clarity in the drawings, such structural features are not shown in a number of the drawings.

The carrier 21 is easily suturable to the cornea (C), as the preserved tissue is quite durable. The interstices within the carrier's collagen matrix, which are not substantially affected by the preferred denaturization, permit host-tissue cells to migrate and grow therein, laying down new collagen which interdigitates to form a "living bond" between the carrier 21 and the cornea (C). The carrier 21 may be of any suitable radial thickness, desirably at least 1 mm to provide sufficient tissue for suturing, and preferably between about 1.5 mm and about 3 mm. As described below, however, the carrier 21 may be substantially larger.

Figure 6:
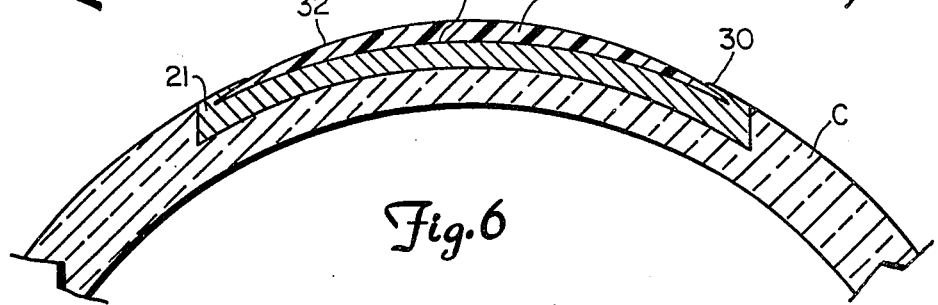
FIG. 6 is a partial cross-sectional view of the cornea of an eye showing lamellar implant of a modified embodiment of the invention.

FIGS. 6-9 show various alternative embodiment of the invention wherein the carrier comprises a disk having a diameter slightly larger than the diameter of the lenticule 22. In FIG. 6, the lenticule 22 is bonded to the carrier 21 which in turn is attached to the cornea (C), initially by sutures and eventually by tissue in growth. This embodiment has the advantage of completely isolating the lenticule from contact with the cornea (C) and the anterior chamber (A). Desirably the peripheral edge of the lenticule 22 is "buried" within the carrier 21 to inhibit growth of epithelium between the two portions of the prosthesis.

Figure 7:
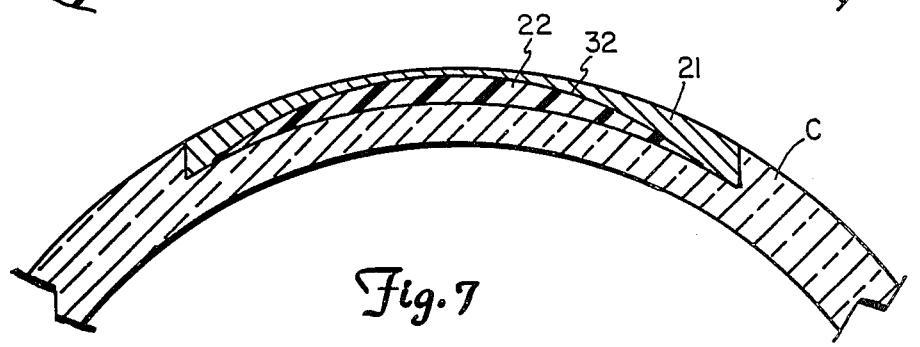
FIG. 7 is a partial cross-sectional view of the cornea of an eye showing lamellar implant of a modified embodiment of the invention.
Figure 8:
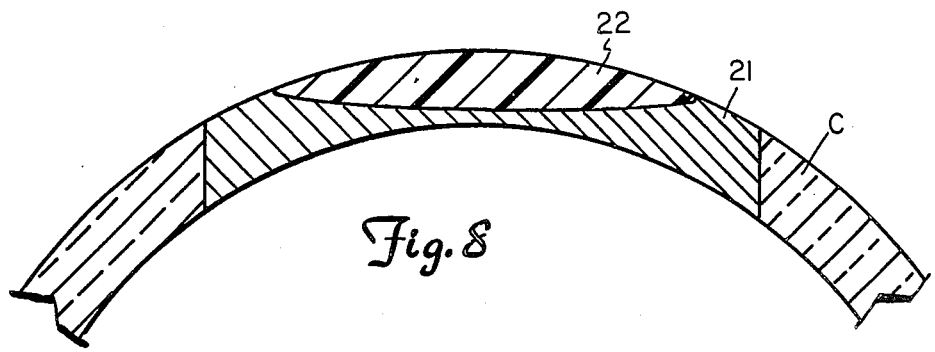
FIG. 8 is a cross-sectional view of a cornea showing a modified embodiment of the invention implanted.
Figure 9:
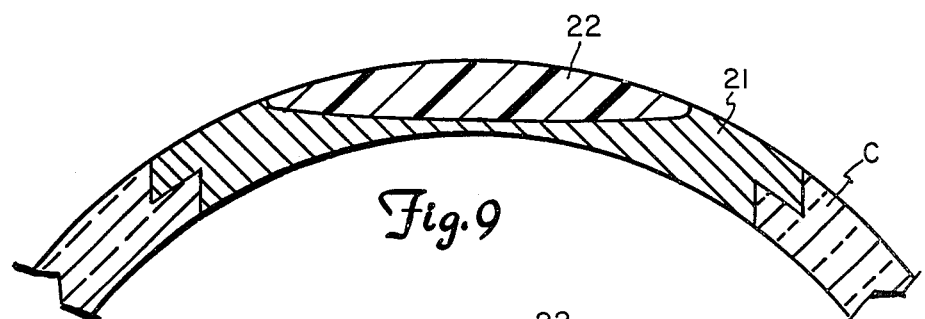
FIG. 9 is a cross-sectional view of a cornea showing a modified embodiment of the invention implanted.

In FIG. 7, the lenticule 22 is held between the carrier 21 and the cornea (C). Similar variations are shown in FIGS. 8 and 9, in which a full thickness of cornea (C) has been removed. It will be recognized that in each of the embodiments shown in FIGS. 6-9, the carrier must be comprised of a tissue which is and remains transparent, i.e., preferably corneal tissue.

Figure 10:
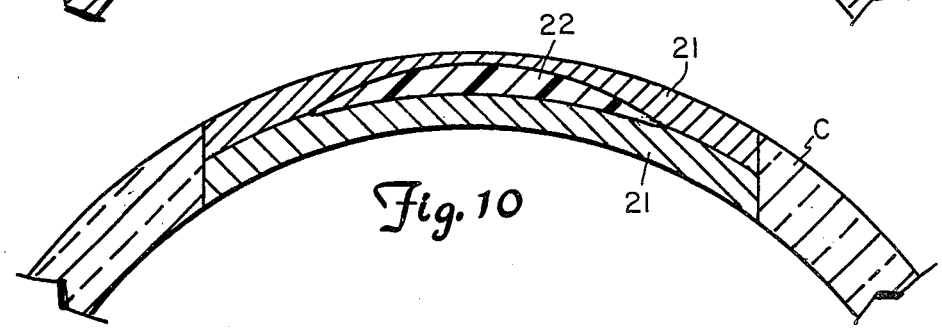
FIG. 10 is a cross-sectional view of a cornea showing a modified embodiment of the invention implanted.
Figure 11:
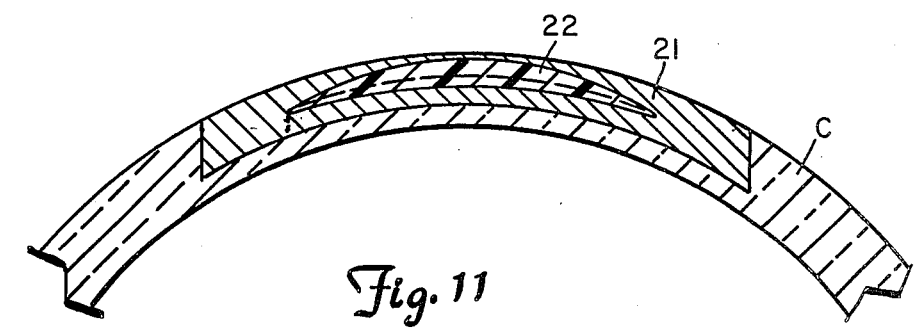
FIG. 11 is a partial cross-sectional view of the cornea of an eye showing lamellar implant of a modified embodiment of the invention.
Figure 12:
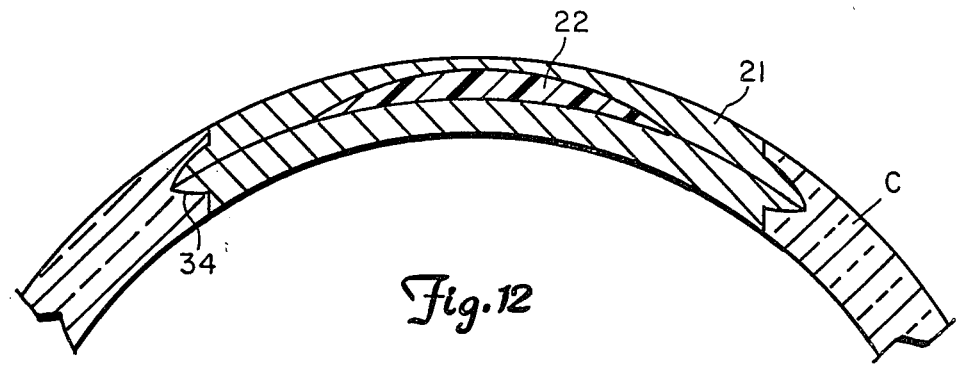
FIG. 12 is a partial cross-sectional view of the cornea of an eye showing lamellar implant of a modified embodiment of the invention.
Figure 13:
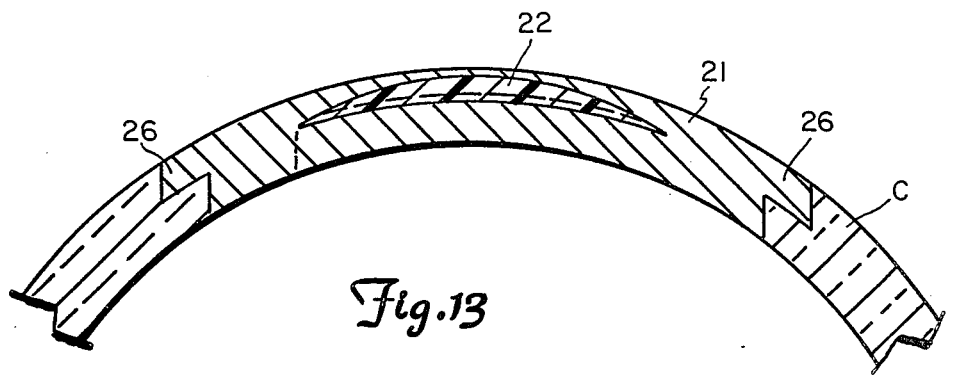
FIG. 13 is a partial cross-sectional view of the cornea of an eye showing lamellar implant of a modified embodiment of the invention.

FIGS. 10-13 show alternative embodiments in which the lenticule 22 is "sandwiched" between layers of the carrier 21. In such embodiments, the carrier may be comprised of two pieces, as shown in FIG. 10, which are optionally bonded, sutured or otherwise fastened together, or alternately the carrier may include a pocket, as shown in FIGS. 11-13, cut so as to receive the lenticule 22 therein. The pocket configuration may be created by known techniques, such as those described in Choyce, "Polysulfone Corneal Inlays to Correct Refractive Errors," *Cataract* 6 (June 1985). Although the "sandwich" technique of FIGS. 10-13 introduces an additional optical interface, it has the advantage of providing a Bowman's membrane which may be re-populated by the recipient's epithelium. Furthermore, this configuration reduces the risk of in growth of epithelium between the preserved tissue and the lenticule. Note that these advantages also apply to the embodiment of FIG. 7.

FIGS. 14-15 depict epikeratoplasty, i.e., placement of the prosthesis on the deepithelized Bowman's membrane of the cornea (C), as described above. Although not depicted in the drawings, protheses of the invention employing the "sandwich" or "pocket" techniques previously described, as well as other modifications of the structura variations shown, may be used in epikeratoplasty.

The surgical methods which are employed for implantation of the prosthesis of the invention are to be very carefully performed, often through the aid of a microscope as is the case with surgical procedures involving donor corneal transplants, nerve reattachments, and other types of microsurgery, and the preparations for surgery and the surgical tools employed in the method of the invention are identical or similar to those employed in a donor corneal trans plant surgery.

Prior to surgery, the diameter of the corneal or epithelial section to be removed from the eye is determined, leaving a sufficient amount of cornea or corneoscleral rim material to enable the prosthesis of the invention to be implanted. Also prior to surgery the prosthesis of the invention is made ready for implantation by suitable sterilization procedures. If desired, the prosthesis may be fabricated at or shortly prior to the time of surgery so that the correct sizing to the individual patient may be accomplished. Alternately the prothesis may be prefabricated in a number of sizes. The diameter of the peripheral portion of the prosthesis, measured across its outer periphery, should be the same as or slightly larger than the diameter across the tissue rim remaining after removal of the corneal portion. Should the patient be a child, care is generally taken to make the diameter of the corneal rim as small as practicable so that, as the child grows, the prosthesis of the invention may be replaced with larger prostheses while still maintaining the field of the implant within the bounds of the corneo-limbus, subsequent implant procedures ordinarily involving the removal of a small portion of the previously formed corneal rim.

In the implant procedure, the eye is immobilized and the corneal portion to be removed is excised employing suitable instruments such as a trephine of the type normally used in corneal transplant procedures. Upon completion of the removal of the corneal tissue, the prosthesis of the invention is inserted into the circular space defined by the rim of the cornea. During the procedure, the prosthesis is supported by a suitable handle or grip such as a small suction cup applied to the outer, domed surface of the lenticule 22. Desirably, small sutures are taken about the periphery of the carrier 21 and are passed through the cornea to anchor the carrier 21 in place. The generally tight fit between the carrier and the corneal tissue rim assures that no leakage of aqueous humor from the eye will occur. Post operative procedures are similar to those commonly employed in corneal transplant surgery.

In another application of the invention, a prosthesis of the invention may be implanted within a pocket surgically formed in the recipient's cornea according to the procedures set forth in Choyce, "Polysulfone Corneal Inlays to Correct Refractive Errors," *Cataract*, 7 (June 1985). In this technique, no cornea is removed, but a pocket is dissected in the cornea and the prosthesis may then be inserted into thepocket. The carrier need not be sutured to the cornea; the preserved tissue will gradually be in grown as described above, firmly fixating the prosthesis.

While a preferred embodiment of the present invention has been described, it should be understood that various changes, adaptations and modifications may be made therein without departing from the spirit of the invention and the scope of the appended claims.

What is claimed is:

1. A corneal implant prosthesis having a transparent lenticule and a carrier attached thereto, the carrier comprising preserved denatured tissue adapted for attachment to an eye.

2. The prosthesis of claim 1 wherein the lenticule is made of biologically acceptable material.

3. The prosthesis of claim 1 wherein the carrier comprises an annular ring, the outer periphery thereof being adapted for attachment to the eye wall, and the inner circumferential surface being attached to the lenticule.

4. The prosthesis of claim 3 wherein the prosthesis is of a thickness suitable for replacement of the full thickness of the eye wall.

5. The prosthesis of claim 3 wherein the carrier includes a radially inwardly extendinq flange received in a complimentary qroove in the lenticule.

6. The prosthesis of claim 5 including a plurality of stakes spaced about the periphery of the lenticule, the stakes extending through a portion of the lenticule into the tissue flange.

7. The prosthesis of claim 7 wherein the preserved tissue has been denatured with formalin or gluteraldehyde.

8. The prosthesis of claim 1 wherein the carrier is of a diameter suitable for attachment to the cornea.

9. The prosthesis of claim 1 wherein the carrier is of a diameter suitable for attachment to the sclera.

10. The prosthesis of claim 1 wherein the carrier is qenerally disk shaped having anterior and posterior surface.

11. A corneal implant prosthesis having a transparent lenticule made of biologically acceptable material, and a carrier bonded thereto, the carrier comprising an annular ring of preserved, denatured biological tissue, the outer periphery of said annular ring being adapted for attachment to the eye wall and the inner circumferential surface thereof being attached to the lenticule.

* * * * *

UNITED STATES PATENT AND TRADEMARK OFFICE
CERTIFICATE OF CORRECTION

PATENT NO. : 4,772,283

DATED : September 20, 1988

INVENTOR(S) : Thomas C. White

It is certified that error appears in the above—identified patent and that said Letters Patent is hereby corrected as shown below:

```
Column 1, line 27, replace "opera" with --opera- -- .
Column 1, line 38, replace "Opthal." with --Ophthal.-- .
Column 1, line 39, replace "Transplan tation," with
     --Transplantation,-- .
Column 1, line 40, replace "Opthal." with --Ophthal.-- .
Column 1, line 47, replace "In stalling" with --Installing-- .
Column 2, line 19, replace "there within" with --therewithin-- .
Column 2, line 27, replace "trans parent" with --transparent-- .
Column 2, line 42, replace "in-qrowth" with --ingrowth-- .
Column 2, line 44, replace "pre-served" with --preserved-- .
Column 2, line 50, replace "cross sectional" with
     --cross-sectional-- .
Column 2, line 57, replace "showinq" with --showing-- .
Column 3, line 34, replace "includinq" with --including-- .
Column 3, line 37, replace "introducinq" with --introducing-- .
Column 3, line 59, replace "analoqously" with --analogously-- .
Column 4, line 5, replace "incompatable" with --incompatible-- .
Column 4, line 5, replace "compatable" with --compatible-- .
Column 4, line 19, replace "includinq" with --including-- .
Column 4, line 20, replace "e.q.," with --e.g.,-- .
Column 4, line 37, replace "thick ness" with --thickness-- .
Column 4, line 45, replace "deepithelized" with --de-epithelized--.
Column 4, line 46, replace "Epikerato plasty" with
     --Epikeratoplasty-- .
Column 4, line 67, replace "extendinq" with --extending-- .
Column 5, line 5, replace "throuqh" with --through-- .
Column 5, line 14, replace "drawinq" with --drawing-- .
Column 5, line 22, replace "anchore" with --anchored-- .
Column 5, line 39, replace flanqe" with --flange-- .
Column 5, line 50, replace "includinq" with --including-- .
Column 5, line 51, replace "co-pendinq" with --co-pending-- .
Column 5, line 54, replace "flanqes" with --flanges-- .
Column 5, line 61, replace "collaqen" with --collagen-- .
```

UNITED STATES PATENT AND TRADEMARK OFFICE
CERTIFICATE OF CORRECTION

PATENT NO. : 4,772,283

DATED : September 20, 1988

INVENTOR(S) : Thomas C. White

It is certified that error appears in the above—identified patent and that said Letters Patent is hereby corrected as shown below:

```
Column 5, lne 63, replace "layinq" with --laying-- .
Column 6, line 37, replace "in growth" with --ingrowth-- .
Column 6, line 42, replace "deepithelized" with --de-epithelized--.
Column 6, line 44, replace "protheses" with --prostheses-- .
Column 6, line 47, replace "structura" with --structural-- .
Column 6, line 53, replace "reattach' with --reattach- -- .
Column 6, line 54, replace "prep" with --prep- -- .
Column 6, line 57, replace "trans plant" with --transplant-- .
Column 6, line 60, replace "leavinq" with --leaving-- .
Column 6, line 67, replace "prothesis" with --prosthesis-- .
Column 7, line 27, replace "Post operative" with
     --Post-operative-- .
Column 7, line 37, replace "thepocket" with --the pocket-- .
Column 8, line 19, replace "extendinq" with --extending-- .
Column 8, line 20, replace "qroove" with --groove-- .
Column 8, line 25, replace "7" with --1-- .
Column 8, line 33, replace "qenerally" with --generally-- .
Column 8, line 34, replace "surface" with --surfaces-- .
```

Signed and Sealed this

Twenty-first Day of March, 1989

Attest:

DONALD J. QUIGG

*Attesting Officer*    *Commissioner of Patents and Trademarks*